United States Patent
Wright et al.

[11] Patent Number: 6,090,120
[45] Date of Patent: Jul. 18, 2000

[54] ARTICULATING ULTRASONIC SURGICAL INSTRUMENT

[75] Inventors: John C. Wright, Loveland, Ohio; Paul J. Smith, West Kingstown, R.I.

[73] Assignee: Ethicon Endo-Surgery, Inc., Cincinnati, Ohio

[21] Appl. No.: 09/255,519

[22] Filed: Feb. 22, 1999

Related U.S. Application Data

[63] Continuation of application No. 09/059,072, Apr. 13, 1998, Pat. No. 5,897,523.

[51] Int. Cl.[7] ..................................................... A61B 17/32
[52] U.S. Cl. ................................................ 606/169; 606/1
[58] Field of Search ................................... 601/2; 604/22; 606/169, 170, 171

[56] References Cited

U.S. PATENT DOCUMENTS

| | | |
|---|---|---|
| 2,990,616 | 7/1961 | Balamuth et al. . |
| 3,053,124 | 9/1962 | Balamuth et al. . |
| 4,108,211 | 8/1978 | Tanaka . |
| 5,058,570 | 10/1991 | Idemoto et al. . |
| 5,203,338 | 4/1993 | Law et al. . |
| 5,275,166 | 1/1994 | Vaitekunas . |
| 5,322,055 | 6/1994 | Davison et al. . |
| 5,324,299 | 6/1994 | Davison et al. . |
| 5,380,274 | 1/1995 | Braddock et al. . |
| 5,405,318 | 4/1995 | Nita . |
| 5,409,498 | 4/1995 | Braddock et al. . |
| 5,505,693 | 4/1996 | Mackool . |
| 5,570,693 | 11/1996 | Jang et al. . |
| 5,596,991 | 1/1997 | Tanaka . |
| 5,762,066 | 6/1998 | Law et al. . |
| 5,873,873 | 2/1999 | Smith et al. ................................. 606/1 |

*Primary Examiner*—Michael Buiz
*Assistant Examiner*—William Lewis
*Attorney, Agent, or Firm*—Bernard Shay

[57] ABSTRACT

A therapeutic ultrasound instrument is described for cutting, dissecting, or cauterizing tissue. Ultrasonic vibrations, when transmitted to organic tissue at suitable energy levels and using a suitable end-effector, may be used for the safe and effective treatment of many medical conditions. An ultrasonic surgical instrument is described which incorporates an articulating end-effector. The instrument comprises an ultrasonic signal generator, an ultrasonically actuated end-effector, and a substantially solid ultrasonic waveguide which connects the ultrasonic signal generator to the end-effector. The waveguide comprises a transmission section extending from the signal generator to a fixed node, and an articulation section extending from the fixed node to an pivoting node. The end-effector includes a waveguide segment. A handle is adapted to hold the signal generator. An outer sheath extends from the handle to the end-effector and surrounds the waveguide. An actuation trigger is rotatably positioned on the handle, and an actuation arm extends from a distal end of the actuation trigger to the pivoting node. The actuation arm is connected to the pivoting node by a lever arm which extends from the pivoting node. Such instruments are particularly suited for use in minimally invasive procedures, such as endoscopic or laparoscopic procedures.

5 Claims, 8 Drawing Sheets

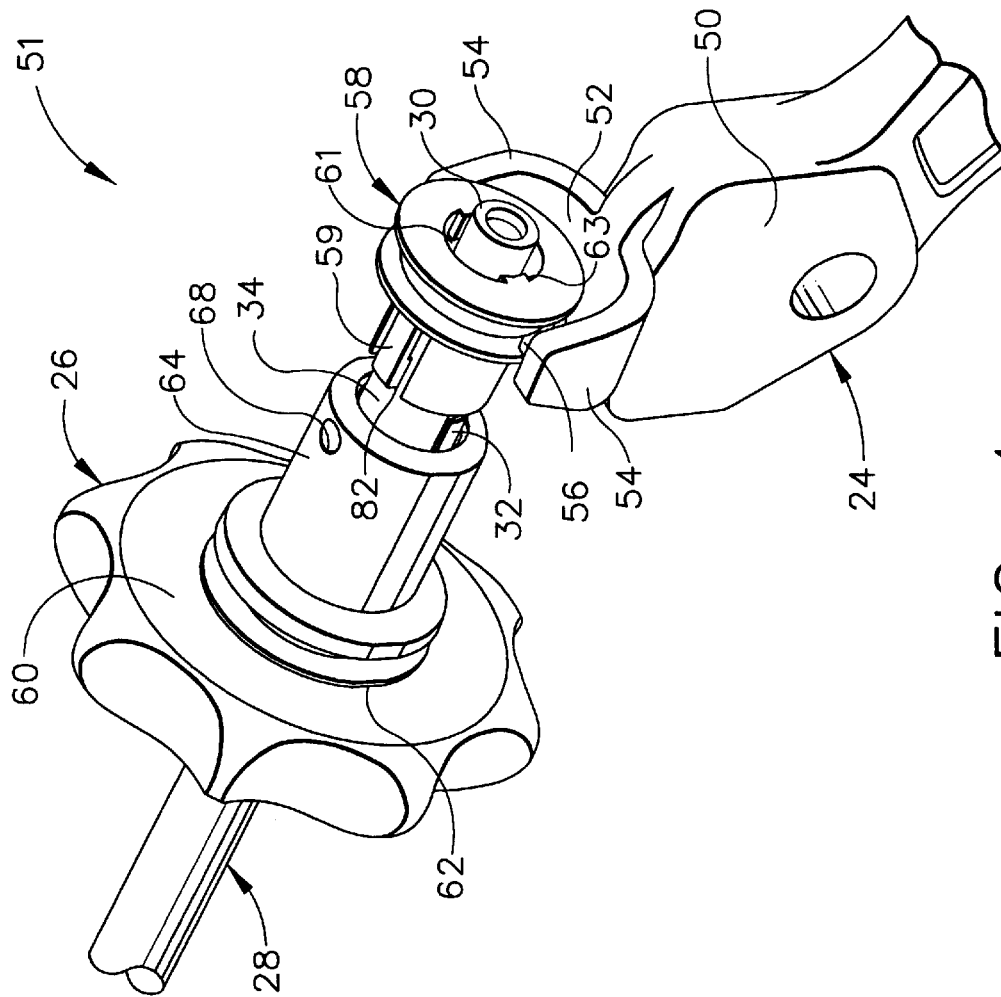
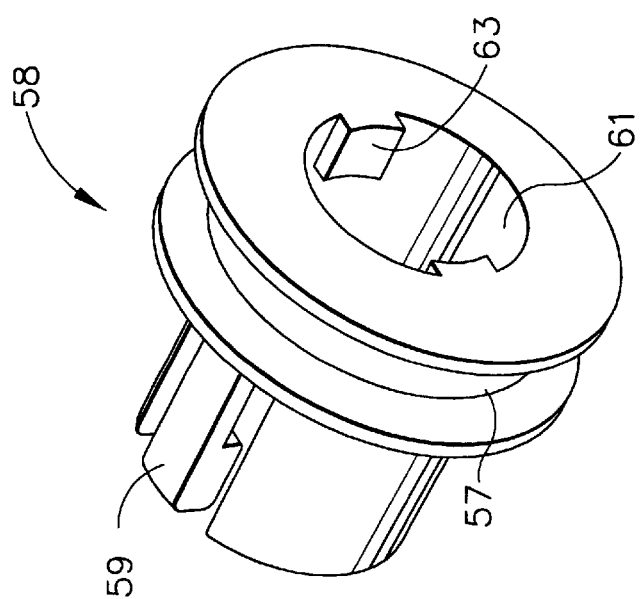
FIG. 4
FIG. 3

ARTICULATING ULTRASONIC SURGICAL INSTRUMENT

This application is a continuation of U.S. patent application No. 09/059,072 which as filed Apr. 13, 1998.

FIELD OF THE INVENTION

The present invention relates, in general, to an ultrasonic surgical instrument and, more particularly, to an ultrasonic surgical instrument incorporating an articulating end-effector.

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy which may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Solid core ultrasonic instruments adapted for use in surgery and, more particularly, for use in minimally invasive surgery, are well known in the art. For example, U.S. Pat. No. 5,322,055 illustrates a clamp coagulator which utilizes solid core ultrasonic technology while U.S. Pat. No. 5,324,299 illustrates an ultrasonic hook blade end-effector for use in surgical applications. In addition, articulating instruments for use in minimally invasive surgery are also known in the art. For example, U.S. Pat. No. 5,409,498 describes an articulating endocutter for use in cutting and stapling tissue. Many ultrasonic surgical instruments used for cutting and coagulation rely upon relatively stiff, solid core ultrasonic waveguides to efficiently deliver energy from the transducer to the end-effector. In such instruments it may be desirable to articulate the end-effector in order to provide the surgeon with flexibility in engaging hard to reach structures. However, the relatively stiff solid core ultrasonic waveguides and the limited structural space available in minimally invasive instruments make it difficult to design appropriate mechanisms for articulating end-effectors in such devices. One option, which is illustrated and described in U.S. patent application Ser. No. 08/770,550 [Attorney Docket No. END-340] which was previously incorporated herein by reference, involves separating the waveguide into two or more segments which may be moved independently to provide articulation.

Flexible high power ultrasonic surgical instruments are also available. Flexible ultrasonic surgical instruments such as atherosclerosis treatment devices, thrombolysis devices, or some stone crushing devices are typically thin wires encased in a polymeric sheath, are relatively flexible, and articulate if assisted with known flexible endoscopy articulation means. For example, U.S. Pat. No. 5,380,274 describes a flexible ultrasonic catheter, and U.S. Pat. No. 4,108,211 describes a flexible endoscope mechanism.

It would, therefore, be advantageous to design an articulating solid core ultrasonic surgical instrument wherein the ultrasonic waveguide is substantially continuous. It would further be advantageous to design a solid core ultrasonic surgical instrument wherein the end-effector was both rotatable and articulatable. It would further be advantageous to design an articulating solid core ultrasonic surgical instrument which could be passed through a trocar or other surgical access device and the end-effector could be articulated utilizing a handle positioned outside of the surgical access device.

SUMMARY OF THE INVENTION

A surgical instrument comprising an ultrasonic signal generator, an ultrasonically actuated end-effector, and a substantially solid ultrasonic waveguide which connects the ultrasonic signal generator to the end-effector. The waveguide comprises a transmission section extending from the signal generator to a fixed node, and an articulation section extending from the fixed node to an pivoting node. The end-effector includes a waveguide segment. A handle is adapted to hold the signal generator. An outer sheath extends from the handle to the end-effector and surrounds the waveguide. An actuation trigger is rotatably positioned on the handle, and an actuation arm extends from a distal end of the actuation trigger to the pivoting node wherein the actuation arm is connected to the pivoting node by a lever arm which extends from the pivoting node.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a perspective view of the articulation collar of the articulation actuation mechanism shown in FIG. 4.

FIG. 4 is a perspective view of an actuation mechanism internal to the surgical instrument shown in FIG. 1.

DETAILED DESCRIPTION OF THE INVENTION

Figure 1:
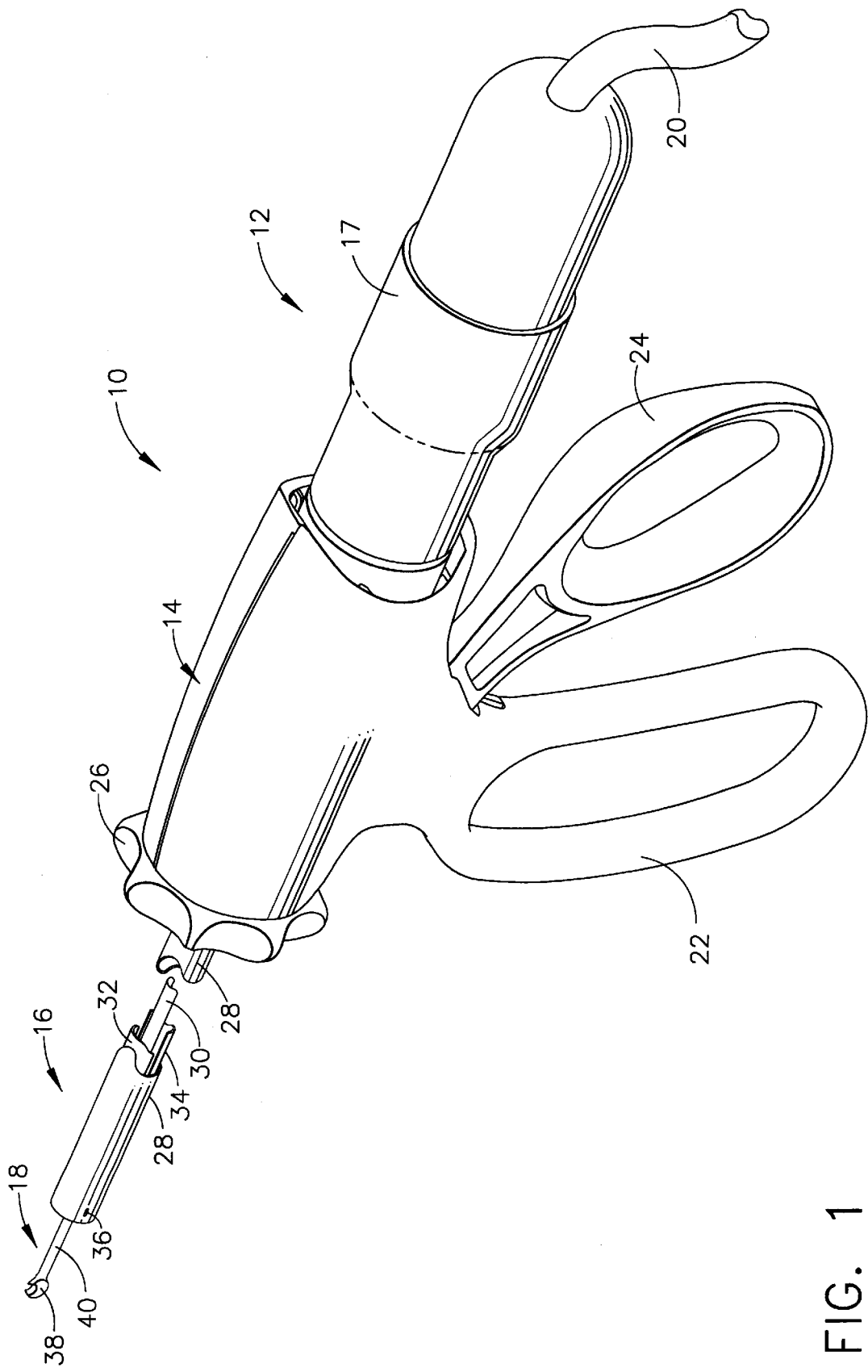
FIG. 1 is a perspective view illustrating a surgical instrument including an articulatable end-effector according to the present invention, wherein the surgical instrument is illustrated in combination with and ultrasonic signal generator.

FIG. 1 is a perspective view illustrating a surgical instrument 10 including an end-effector 18 which may be articulated according to the present invention. In FIG. 1, surgical instrument 10 is illustrated in combination with ultrasonic signal generator 12. Ultrasonic surgical instrument 10 includes instrument handle 14, ultrasonic transmission rod assembly 16 and ultrasonic effector 18. Ultrasonic signal generator 12 includes generator housing 17 and power supply cable 20. Ultrasonic surgical generator 12, which may also be referred to as a handpiece, comprises a housing 17, housing a transducer, preferably a piezeoceramic transducer, for converting an electrical signal, for example, a 55,000 Hz sinusoidal waveform, into a mechanical longitudinal vibration. A suitable ultrasonic signal generator is available from Ethicon Endo-Surgery, Inc. as make ULTRA-CISION® and model HP051. Instrument handle 14 includes finger grip 22, actuation trigger 24 and rotation knob 26. Ultrasonic transmission rod assembly 16 includes outer sheath 28, ultrasonic waveguide 30, mounting arm 32, actuating arm 34 and pivot slot 36. End-effector 18 includes hook blade 38 and waveguide segment 40.

Figure 2:
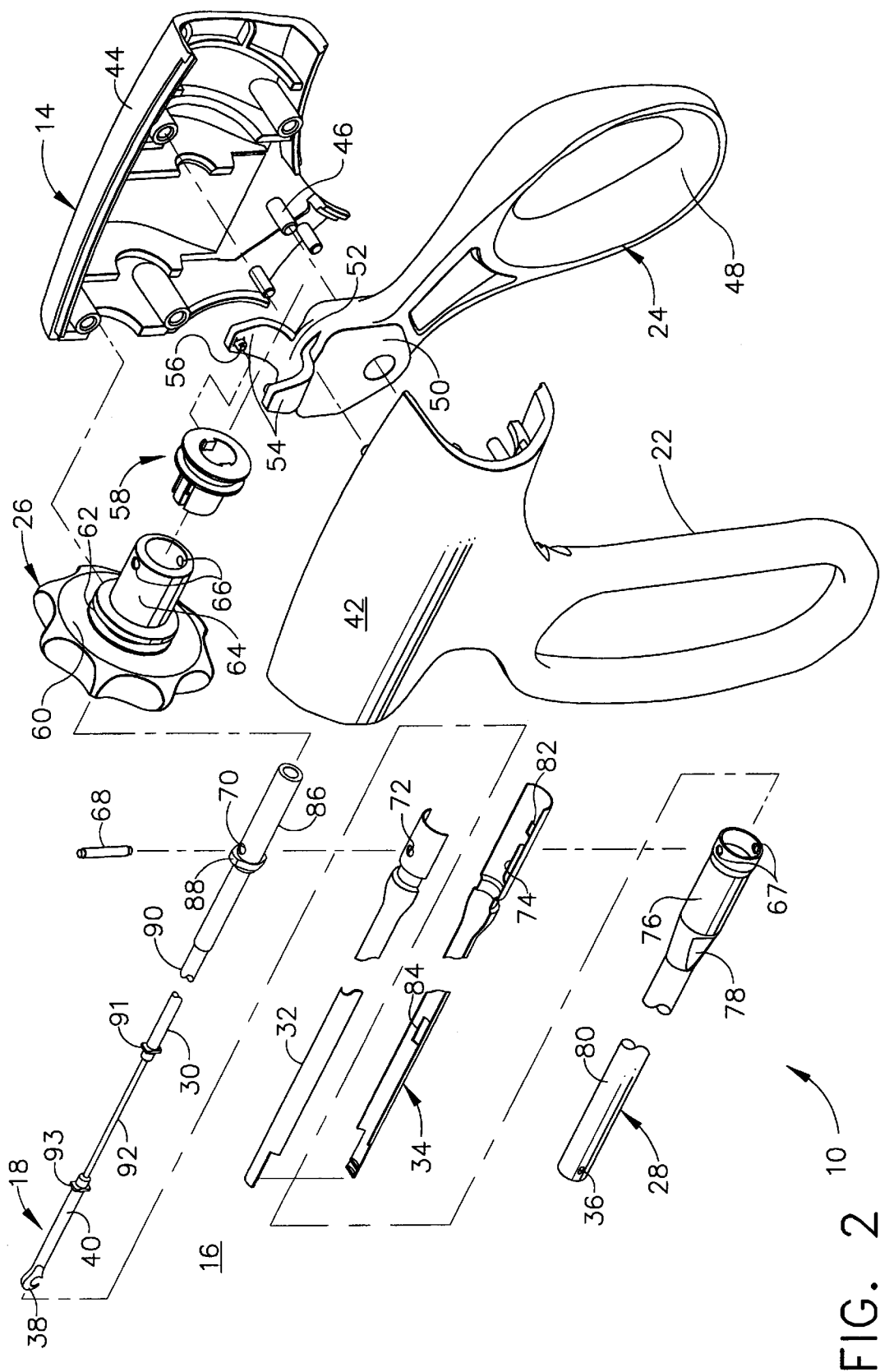
FIG. 2 is an exploded perspective view of a surgical instrument according to the present invention.

FIG. 2 is an exploded perspective view of surgical instrument 10. FIG. 2 illustrates the elements and interconnection of instrument handle 14, ultrasonic transmission rod assembly 16 and ultrasonic end-effector 18. Instrument handle 14 includes left housing half 42 and right housing half 44. Left housing half 42 includes finger grip 22. Actuation trigger 24 is rotatably mounted on pivot pin 46 between left housing half 42 and right housing half 44. Actuation trigger 24 includes thumb ring 48, pivot 50, yoke 52, yoke arms 54 and detent pins 56. Articulation collar 58 is positioned in yoke 52 and rotatably engaged by detent pins 56. Rotation knob 26 is rotatably positioned between left housing half 42 and right housing half 44 at the distal end of instrument handle 14. Rotation knob 26 includes rotation disk 60, rotation channel 62, rotation drive tube 64 and rotation knob connector pin holes 66. The proximal end of ultrasonic transmission rod assembly 16 is connected to rotation knob 26 by rotation connector pin 68.

In FIG. 2 ultrasonic transmission rod assembly 16 includes outer sheath 28, ultrasonic waveguide 30, mounting arm 32 and actuating arm 34. Outer sheath 28 is affixed to ultrasonic waveguide 30, mounting arm 32, actuating arm 34 and rotation drive tube 64 by rotation connector pin 68 which passes through rotation knob connector pin holes 66, waveguide connector pin hole 70, outer sheath connector pin holes 67, waveguide connector pin hole 70, mounting arm connector pin hole 72, and actuation arm connector pin slot 74. Outer sheath 28 includes proximal tube 76, wrench flats 78 and waveguide support tube 80. Waveguide support tube 80 includes one or more pivot slots 36 which are positioned at a distal end of waveguide support tube 80. Mounting arm 32 and actuating arm 34 are positioned within and extend from the proximal to the distal end of outer sheath 28. Actuating arm 34 includes actuation arm connector pin slot 74 and actuation slot 82 at the proximal end thereof and distal slot 84 at a distal end thereof. Actuation arm 34 is adapted to engage articulation collar 58. Mounting arm 32 and actuating arm 34 are positioned on either side of ultrasonic waveguide 30 within outer sheath 28.

In FIG. 2 ultrasonic waveguide 30 includes node isolator 88, connector segment 86, transmission segment 90 and articulation segment 92. Articulation segment 92 is bounded by fixed node 91 at the proximal end thereof and pivoting node 93 at the distal end thereof. Waveguide segment 40 of ultrasonic end-effector 18 is connected to ultrasonic waveguide 30 at pivoting node 93. The distal end of waveguide segment 40 is connected to hook blade 38. Articulation segment 92 is generally thinner than transmission segment 90 and, more particularly, preferably has a diameter of 20 to 70 percent of the diameter of the narrowest portion of transmission segment 90. In addition, or as an alternative, articulation segment 92 may include a bend or curve to facilitate rotational movement of pivoting node 93. Rotation is facilitated by reducing the force required to bend articulation segment 92. Ultrasonic waveguide 30 is preferably fabricated from a solid core shaft constructed out of material which propagates ultrasonic energy efficiently, such as a titanium alloy (e.g., Ti-6A1-4V) or an aluminum alloy.

FIG. 3 is a detailed perspective view of articulation collar 58. As illustrated in FIG. 3, articulation collar 58 includes collar rotation channel 57, collar latch 59, collar central aperture 61 and collar guide flanges 63.

FIG. 4 is a detailed perspective view of handle actuation mechanism 51 of surgical instrument 10. In handle actuation mechanism 51, actuation trigger 24 is pivotally connected to articulation collar 58 by yoke 52. Yoke arms 54 of yoke 52 spring load detent pins 56 in collar rotation channel 57. The proximal end of ultrasonic waveguide 30 extends through central aperture 61 of articulation collar 58. The proximal end of actuating arm 34 extends into collar central aperture 61 of articulation collar 58. Collar latch 59 of articulation collar 58 engages actuation slot 82 which is positioned at the proximal end of actuating arm 34. Collar guide flanges 63 of articulation collar 58 support and align the proximal end of ultrasound transmission rod assembly 16. The proximal ends of ultrasonic waveguide 30 and mounting arm 32 are rotationally and axially affixed to rotation knob 26 by rotation connector pin 68 which passes through rotation drive tube 64. The proximal end of actuating arm 34 is rotationally affixed to rotation knob 26 by rotation connector pin 68 which passes through rotation drive tube 64 and actuation arm connector pin slot 74 of actuating arm 34.

Figure 5:
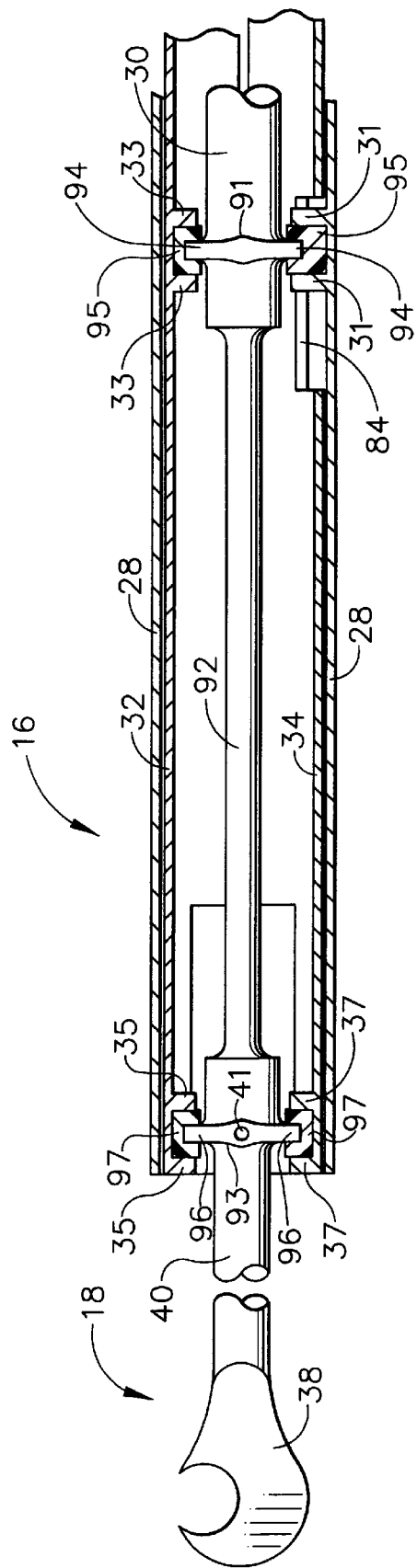
FIG. 5 is a side sectional view illustrating the distal end of the ultrasonic transmission rod assembly of a surgical instrument according to the present invention.

FIG. 5 is a side sectional view illustrating the distal end of ultrasonic transmission rod assembly 16 and end-effector 18 of surgical instrument 10. In FIG. 5, fixed node 91 includes mounting flanges 94 which are positioned in isolation mounts 95. Isolation mounts 95 are positioned between and held in place by rigid flanges 31 on the interior of outer sheath 28 and rigid flanges 33 on mounting arm 32. Distal slot 84 in actuation arm 34 is positioned such that mounting flange 94 passes through distal slot 84 to isolation mount 95. Pivoting node 93 includes mounting flanges 96 which are positioned in isolation mounts 97. Mounting flanges 96 may be referred to, either alone or in combination, as a rotational flange. Isolation mounts 97 are positioned between and held in place by rigid flanges 35 on mounting arm 32 and rigid flanges 37 on actuating arm 34. Isolation mounts 95 and 97 are typically constructed of an elastomeric material, such as silicone rubber.

Figure 6:
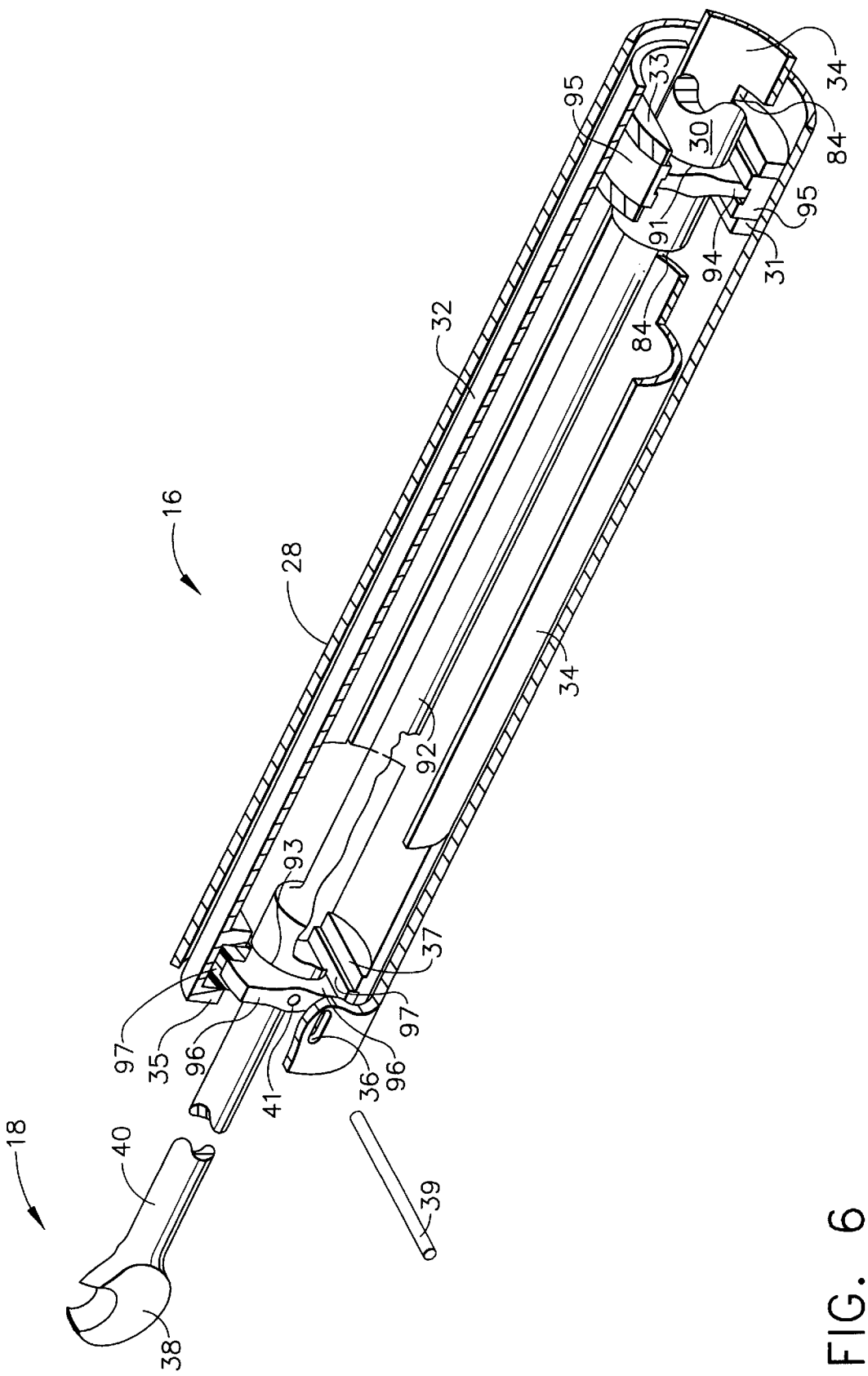
FIG. 6 is a cutaway perspective view illustrating a distal portion of the ultrasonic transmission rod assembly of a surgical instrument according to the present invention.

FIG. 6 is a cutaway perspective view illustrating a distal portion of ultrasonic transmission rod assembly 16 and end-effector 18 of surgical instrument 10. In FIG. 6, articulation pivot pin 39 passes through pivot slot 36 and pivot hole 41 which passes through ultrasonic waveguide 30 at pivoting node 93.

Figure 7:
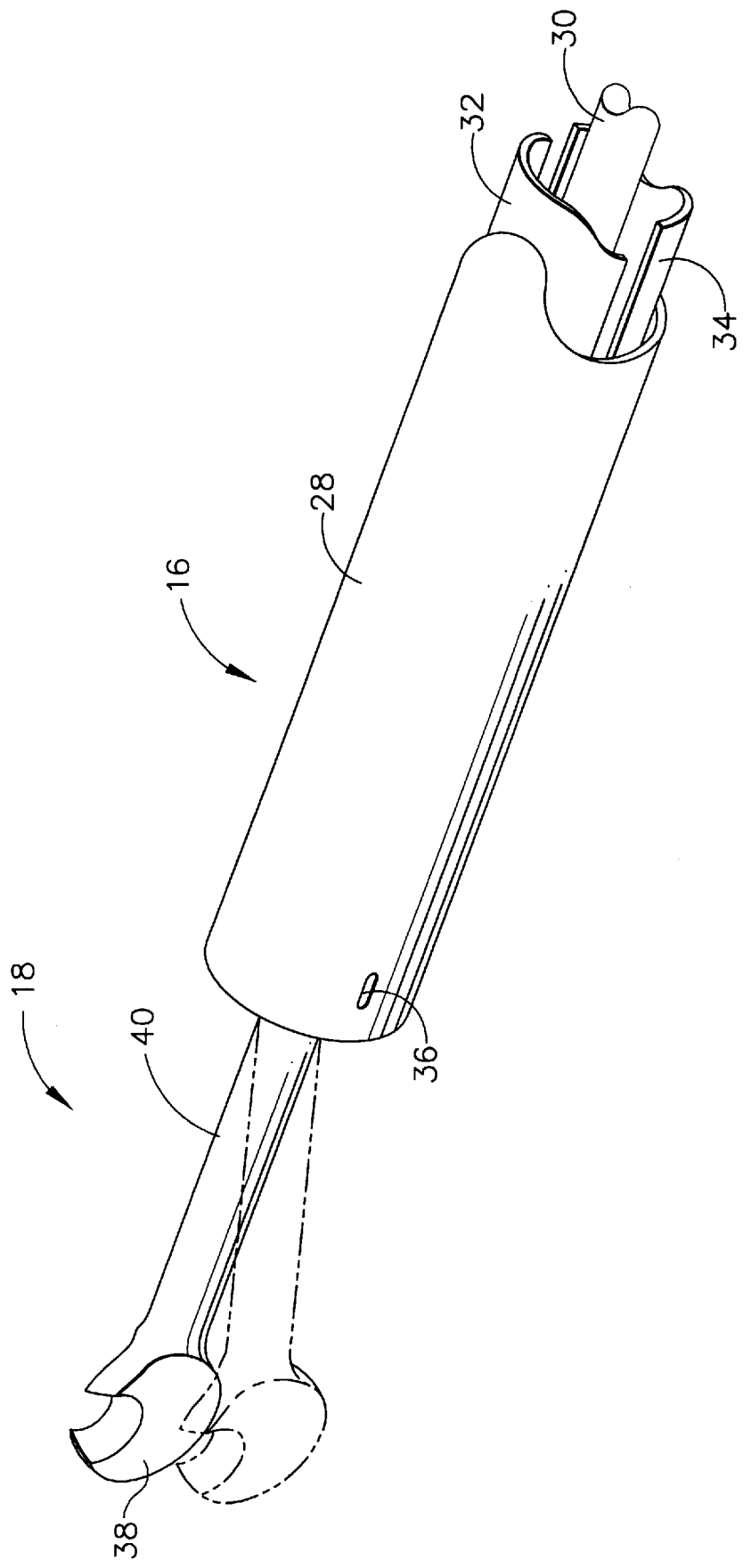
FIG. 7 is a perspective view illustrating a distal portion of the ultrasonic transmission rod assembly of a surgical instrument according to the present invention wherein the articulated position of the end-effector is shown in phantom.
Figure 8:
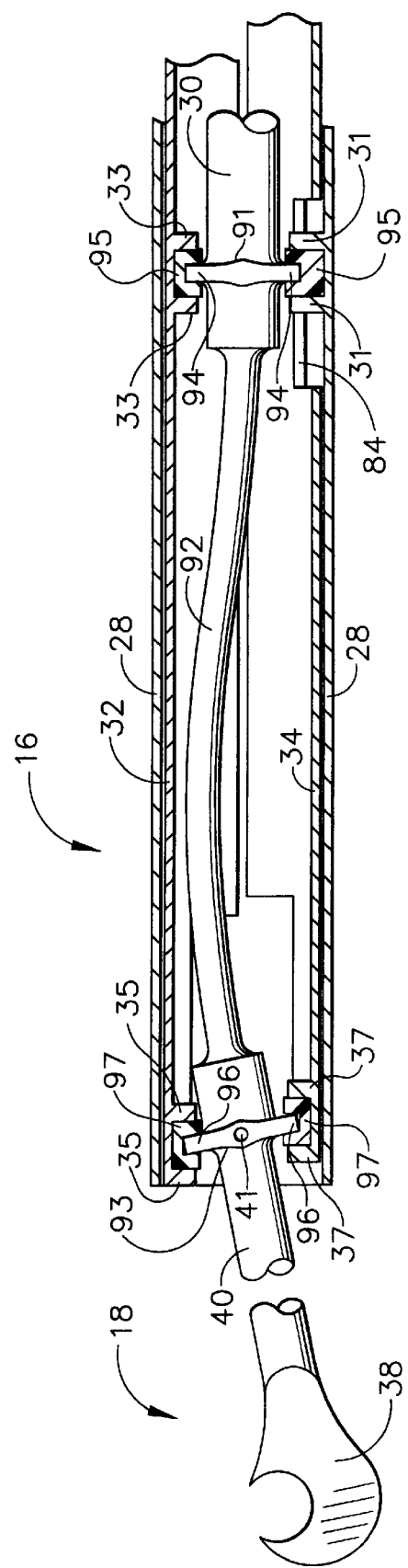
FIG. 8 is a side sectional view illustrating the distal end of the ultrasonic transmission rod assembly of a surgical instrument according to the present invention with the end-effector in the articulated position.
Figure 9:
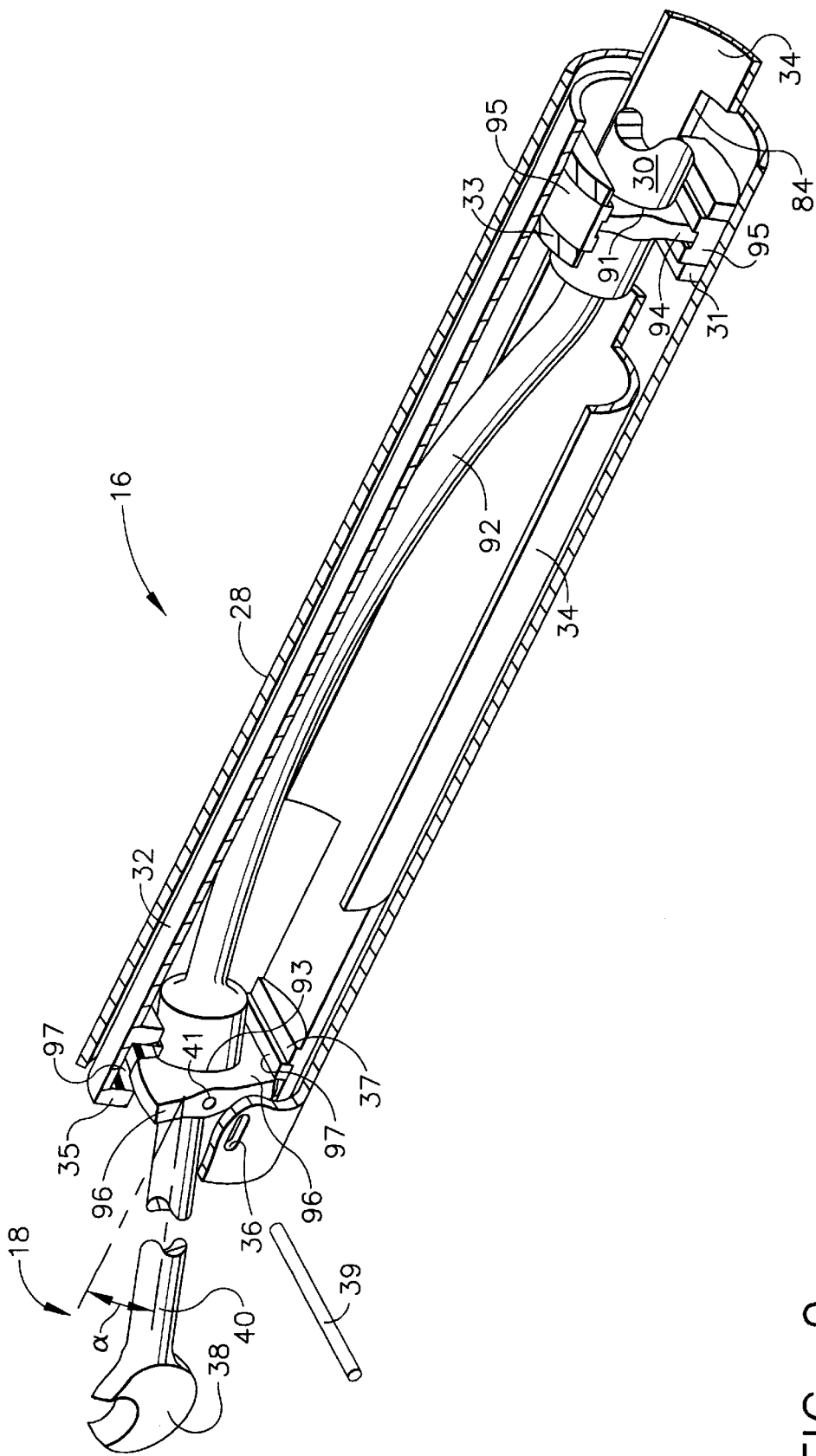
FIG. 9 is a cutaway perspective view illustrating a distal portion of the ultrasonic transmission rod of a surgical instrument according to the present invention with the end-effector in the articulated position.

The operation of a surgical instrument according to the present invention may now be described in detail. FIG. 7 is a perspective view illustrating a distal portion of ultrasonic transmission rod assembly 16 of surgical instrument 10 according to the present invention wherein the articulated position of end-effector 18 is shown in phantom. FIG. 8 is a side sectional view illustrating the distal end of the ultrasonic transmission rod assembly 16 and end-effector 18 of surgical instrument 10 according to the present invention with end-effector 18 in its articulated position. FIG. 9 is a cutaway perspective view illustrating a distal portion of ultrasonic transmission rod assembly 16 of surgical instrument 10 according to the present invention with end-effector 18 in its articulated position.

In operation, end-effector 18 may be articulated by moving actuation trigger 24 of instrument handle 14 toward finger grip 22. When actuation trigger 24 is moved toward finger grip 22, pivot 50 of actuation trigger 24 pivots on pivot pin 46, forcing yoke 52 to move toward the proximal end of instrument handle 14. Proximal movement of yoke 52 is transmitted to articulation collar 58 by yoke arms 54 and detent pins 56 which engage articulation collar 58 in collar rotation channel 57. Thus when actuation trigger 24 is moved toward finger grip 22, articulation collar 58 is moved axially in a distal to proximal direction.

Axial movement of articulation collar 58 is transmitted to actuating arm 34 by collar latch 59 which engages actuation slot 82 in actuating arm 34. Actuation arm connector pin slot 74 in actuating arm 34 is elongated to ensure that rotation connector pin 68 and node isolator 88 do not interfere with the axial movement of actuating arm 34. Similarly, distal slot 84 in actuating arm 34 is elongated to ensure that rigid flanges 31, mounting flange 94 and isolation mount 95 do not interfere with the axial movement of actuating arm 34. Thus, distal to proximal axial movement of articulation collar 58 forces actuating arm 34 to move axially in a distal to proximal direction and, since articulation collar 58 is free to move axially with respect to the proximal end of ultrasonic waveguide 30, axial movement of actuating arm 34 does not result in axial movement of the proximal nd of ultrasonic waveguide 30.

Articulation is accomplished by the relative axial movement of the proximal end of actuating arm 34 with respect to the proximal end of ultrasonic waveguide 30 while the distal end of actuating arm 34 is fixed to at least one side of the distal end of ultrasonic waveguide 30 at the distal end of articulation segment 92. Mounting flanges 94 are rigidly affixed to ultrasonic waveguide 30 at fixed node 91, which is positioned at the proximal end of articulation segment 92 while mounting flanges 96 are rigidly affixed to ultrasonic waveguide 30 at pivoting node 93, which is positioned at the distal end of articulation segment 92. Fixed node 91 is held in place by mounting flanges 94 which are positioned in isolation mounts 95. Isolation mounts 95 are held in place by rigid flanges 31 on mounting arm 32 and by rigid flanges 33 on outer sheath 28. Pivoting node 93 is pivoted around articulation pivot pin 39 by the rotational force exerted on mounting flanges 96 when actuating arm 34 is moved axially in a distal to proximal direction. Mounting flanges 96 are positioned in isolation mounts 97 which are held in place by rigid flanges 35 on mounting arm 32 and by rigid flanges 37 on actuating arm 34. Thus, distal to proximal axial movement of actuating arm 34 moves rigid flanges 37 and isolation mount 97 in a distal to proximal direction, applying a force to one mounting flanges 96. However, since the opposite one of mounting flanges 96 is held fixed by mounting arm 32, the force applied to pivoting node 93 is substantially rotational. Thus, with fixed node 91 held firmly in place and a rotational force applied to pivoting node 93, the force applied to articulation segment 92 by the axial movement of actuating arm 34 will tend to force articulation segment 92 to flex away from actuating arm 34, allowing pivoting node 93 to pivot around articulation pivot pin 39 and end-effector 18 to articulate as illustrated in FIGS. 7, 8 and 9.

In order to properly position end-effector 18 prior to or after it is articulated, surgical instrument 10 is also adapted to allow end-effector 18 to be rotated around a central axis. Axial rotation of end-effector 18 is accomplished by moving rotation knob 26. When rotation disk 60 of rotation knob 26 is rotated, rotational force is transmitted through rotation drive tube 64 to rotation connector pin 68. As illustrated in FIG. 2, rotation channel 62 is mounted between left housing half 42 and right housing half 44 such that rotation knob 26 may be freely rotated but will not move axially with respect to instrument handle 14. Rotation connector pin 68 passes through rotation knob connector pin holes 66, outer sheath connector pin holes 67, mounting arm connector pin hole 72, waveguide connector pin hole 70 and actuation arm connector pin slot 74, thus transmitting rotational forces from rotation knob 26 to outer sheath 28, mounting arm 32, ultrasonic waveguide 30 and actuating arm 34. Rotational forces are, in turn transmitted back to articulation collar 58 by the interconnection of actuation slot 82 and collar latch 59. Rotational forces are transmitted to end-effector 18 by ultrasonic waveguide 30 which is rigidly affixed to waveguide segment 40 at pivoting node 93. Collar rotation channel 57 may be adapted to include detents (not shown) which, in conjunction with detent pins 56 may be used to rotationally position end-effector 18 and to prevent inadvertent rotational movement of end-effector 18.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:

a handle;

a surgical end-effector;

an ultrasonic transmission wire assembly operatively coupled between said handle and said surgical end-effector, wherein said transmission wire assembly comprises:

a proximal and a distal end, wherein said proximal end of said ultrasonic transmission wire assembly is coupled to said distal end of said ultrasonic transmission wire assembly and said distal end of said ultrasonic transmission wire assembly is coupled to said surgical end-effector; and an actuating element extending from said handle to said distal end of said transmission wire assembly, wherein said actuating element is operatively connected to said end-effector and to said handle, and wherein said ultrasonic transmission wire assembly is fixed at a said proximal end and rotatable at said distal end.

2. An ultrasonic surgical instrument comprising:

a handle;

a surgical end-effector;

an ultrasonic transmission wire assembly operatively coupled between said handle and said surgical end-effector, wherein said transmission wire assembly comprises:

a proximal and a distal end, wherein said proximal end of said ultrasonic transmission wire assembly is coupled to said distal end of said ultrasonic transmission wire assembly and said distal end of said ultrasonic transmission wire assembly is coupled to said surgical end-effector; and an actuating element extending from said handle to said distal end of said transmission wire assembly, wherein said actuating element is operatively connected to said end-effector and to said handle;

an outer sheath having a proximal end and a distal end and surrounding said ultrasonic transmission wire assembly, said outer sheath terminating proximal to said end-effector, wherein said outer sheath extends from said handle to said distal end of said ultrasonic transmission wire assembly;

a mounting flange positioned at said proximal end of said ultrasonic transmission wire assembly, said mounting flange being fixed to an interior surface of said outer sheath; and a rotation flange positioned at said distal end of said ultrasonic transmission wire assembly wherein said rotation flange is attached to said ultrasonic transmission wire assembly and said actuating element.

3. An ultrasonic surgical instrument according to claim 2 wherein said ultrasonic transmission wire assembly is fixed at a said proximal end and rotatable at said distal end.

4. An ultrasonic surgical instrument comprising:

a handle;

a surgical end-effector;

an ultrasonic transmission wire assembly operatively coupled between said handle and said surgical end-effector, wherein said ultrasonic transmission wire assembly comprises:

an articulating ultrasonic waveguide segment having a proximal end and a distal end, wherein said proximal end of said articulating ultrasonic waveguide segment is coupled to said distal end of said ultrasonic transmission wire assembly and said distal end of said articulating ultrasonic waveguide segment is coupled to said surgical end-effector; and an actuating element extending from said handle to said distal end of said ultrasonic transmission wire assembly, wherein said actuating element is operatively connected to said articulating ultrasonic waveguide segment and to said handle;

an outer sheath having a proximal end and a distal end and surrounding said ultrasonic transmission wire assembly and said actuating element, wherein said outer sheath extends from said handle to said distal end of said ultrasonic transmission wire assembly; and a rotation flange positioned at said distal end of said ultrasonic transmission wire assembly wherein said rotation flange is attached to said ultrasonic transmission wire assembly and said actuating element.

5. An ultrasonic surgical instrument according to claim 4 wherein said ultrasonic transmission wire assembly is fixed at said proximal end and rotatable at said distal end.

* * * * *